United States Patent [19]
Greve

[11] Patent Number: 5,067,951
[45] Date of Patent: Nov. 26, 1991

[54] OPHTHALMOLOGIC APPARATUS

[75] Inventor: Peter Greve, Essingen, Fed. Rep. of Germany

[73] Assignee: Carl-Zeiss-Stiftung, Heidenheim, Fed. Rep. of Germany

[21] Appl. No.: 404,099

[22] Filed: Sep. 7, 1989

[30] Foreign Application Priority Data

Sep. 7, 1988 [DE] Fed. Rep. of Germany ....... 3830378

[51] Int. Cl.$^5$ ............................................. A61N 5/06
[52] U.S. Cl. .................................... 606/004; 606/18; 128/395; 351/209; 351/221
[58] Field of Search ........................................ 606/4–6, 606/18; 128/395, 397, 398; 351/205–244

[56] References Cited

U.S. PATENT DOCUMENTS

| | | | |
|---|---|---|---|
| 3,614,662 | 10/1971 | Monchamp et al. | 331/94.5 |
| 3,906,393 | 9/1975 | Fletcher et al. | 350/161 |
| 4,520,816 | 6/1985 | Scharchar et al. | 606/4 |
| 4,719,912 | 1/1988 | Weinberg | 606/4 |
| 4,764,930 | 8/1988 | Bille et al. | 372/23 |

FOREIGN PATENT DOCUMENTS

| | | | |
|---|---|---|---|
| 0164751 | 12/1985 | European Pat. Off. | 606/13 |
| 230094 | 7/1987 | European Pat. Off. | 606/4 |
| WO86/06610 | 11/1986 | PCT Int'l Appl. | 606/4 |

OTHER PUBLICATIONS

"Semiconductor Laser Endophotocoagulation of the Retna" by Puliafito et al; Arch Ophthalmol, vol. 105, Mar. 1987.

"YAG Laser Ophthalmic Microsurgery" by Trokel Appleton Century-Crofts/Norwalk, Conn. 1984, pp. 39–47.

Primary Examiner—David Shay
Attorney, Agent, or Firm—Walter Ottesen

[57] ABSTRACT

The invention is directed to an ophthalmologic apparatus which includes a laser module which permits microsurgery with pulsed radiation as well as coagulation therapy by means of continuous-wave radiation.

2 Claims, 1 Drawing Sheet 5,067,951

OPHTHALMOLOGIC APPARATUS

FIELD OF THE INVENTION

The invention relates to an ophthalmologic apparatus for conducting a coagulation treatment on a patient by means of continuous-wave laser radiation and for performing microsurgery on the patient by means of pulsed laser radiation.

BACKGROUND OF THE INVENTION

Essentially two types of laser are utilized in ophthalmology, namely, Ar/Kr gas discharge laser for coagulation which is driven by steady power in continuous-wave operation in the range of several watts as well as pulsed Nd-YAG-laser for microsurgery which is driven by pulsed energy in the mJ-range. Since both types of laser are each operated in only one operational mode, namely, continuous-wave driven or pulse driven, their use in ophthalmology leads to respective individual apparatus configurations which are more or less complex. Combination apparatus which are suitable for coagulation as well as for microsurgery can only be realized by combining the above-mentioned laser devices on an ophthalmologic apparatus such as a slit lamp and are technically complex and correspondingly expensive.

SUMMARY OF THE INVENTION

It is an object of the invention to provide an apparatus configuration which permits microsurgery by means of pulsed radiation as well as coagulation therapy by continuous-wave radiation with only one laser module. It is a further object of the invention to provide such an apparatus configuration which is physically small and technically less complicated than known apparatus for this purpose.

The ophthalmologic apparatus of the invention is for conducting a coagulation treatment and for performing microsurgery on a patient. The apparatus includes a frame and a single laser module mounted on this frame. According to a feature of the invention, the laser module has at least one semiconductor laser diode for selectively generating continuous-wave laser radiation for performing the coagulation treatment and pulsed laser radiation for performing the microsurgery.

Semiconductor laser diodes can be pulse driven as well as continuous-wave driven. The emitted wavelength in the range of 770 to 810 nm is well suited for coagulation purposes on the ocular fundus. Continuous-wave capacities in the range of 200 to 500 mw are obtainable without complex equipment and with further means, up to 2 watts are obtainable. In this way, adequate capacity is available for coagulation. Average capacities of 1 watt are the norm with semiconductor laser diodes in pulsed operation. This corresponds to pulse energies of up to 50 mJ at a 10 to 20 Hz repetition rate and a pulse width of 10 ns which is sought after. This is adequate for microsurgical applications on the eye. The operation of a laser diode in continuous-wave operation as well as in pulsed operation is possible via a power supply. The laser radiation can be focussed in the anterior eye structures or on the ocular fundus with the variable optic.

In an advantageous embodiment of the invention, the laser module is mounted above the viewing microscope of a slit lamp and the laser radiation is directed via a manipulator mirror onto the eye to be treated.

The advantages achieved with the invention are especially seen in that by utilizing a single laser source for continuous-wave radiation as well as for pulsed radiation, an especially convenient and simple overall configuration of the apparatus is obtained. A maintenance-free overall system is possible because the laser source is sufficient without parts which wear such as flash lamps or discharge tubes.

BRIEF DESCRIPTION OF THE DRAWING

The invention will now be described with reference to FIG. 1 of drawing which shows the inventive arrangement of a laser module mounted on a slit lamp.

DESCRIPTION OF THE PREFERRED EMBODIMENTS OF THE INVENTION

Figure 1:
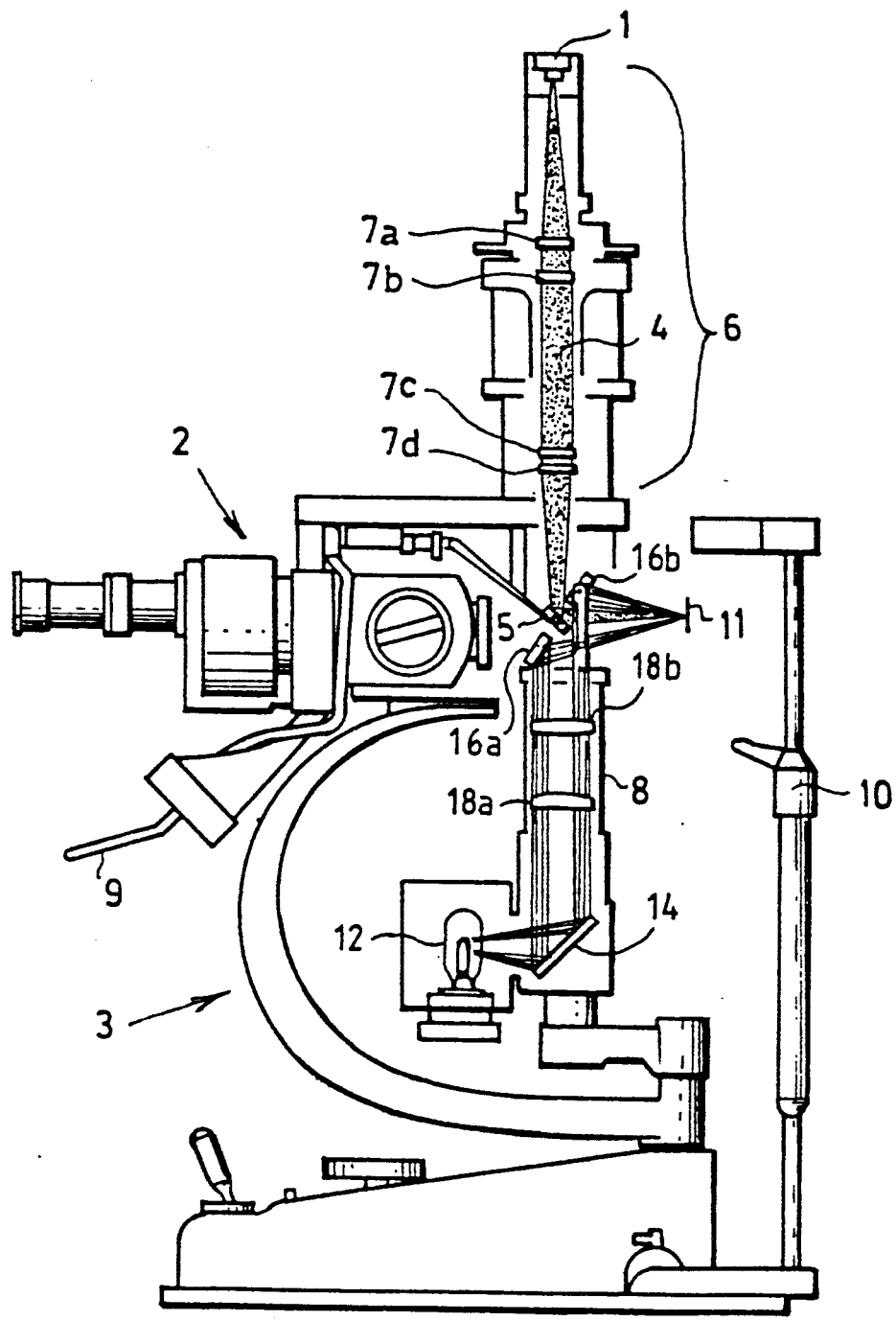

Reference numeral 6 identifies a laser module which contains semiconductor laser diodes 1. The required power supply for driving the semiconductor laser diodes is not shown in the drawing; however, this power supply can be a commercially available unit.

A semiconductor laser diode 1 is shown at the uppermost location on the laser module 6. The laser radiation is expanded via lenses (7a to 7d) and is deflected at a manipulator mirror 5 which is arranged in the beam path 8 of a conventional slit lamp 3 having a light source 12. The slit lamp 3 also includes deflecting mirrors (14, 16a, 16b) and lenses (18a, 18b) which conjointly define the beam path 8. Reference numeral identifies the handle for actuating the manipulator mirror 5 and reference numeral 2 identifies the viewing microscope of the slit lamp. A head support 10 is provided for the patient. The laser beam 4 and the illuminating beam of the slit lamp are focussed at the position 11 of the patient's eye.

It is understood that the foregoing description is that of the preferred embodiments of the invention and that various changes and modifications may be made thereto without departing from the spirit and scope of the invention as defined in the appended claims.

What is claimed is:

1. An ophthalmologic apparatus for conducting a coagulation treatment and for performing microsurgery on an eye of a patient, the apparatus comprising:

a frame defining first and second mounting structures in substantial alignment with each other;

a slit lamp mounted on said first mounting structure and including: a light source means for supplying light; a lens assembly defining a first optical axis; and, mirror means straddling said first optical axis so as to define a clear opening therethrough along said axis;

said lens assembly and said mirror means conjointly defining a beam path along which the light of said light source means is directed toward the eye of the patient;

a laser module having at least one semiconductor laser diode means for selectively generating continuous-wave laser radiation for performing the coagulation treatment and pulsed laser radiation for performing the microsurgery, the laser module having a lens unit means for defining a second optical axis along which the laser radiation travels;

said lens unit means being mounted on said second mounting structure to cause said second optical axis to be coincident with said first optical axis to conjointly define a common axis therewith and to permit said laser radiation to pass through said opening; and, a manipulator mirror pivotally mounted on said frame and at a predetermined location on said common axis for deflecting the laser radiation out of said common axis and toward the eye of the patient requiring treatment or surgery.

2. The ophthalmologic apparatus of claim 1, said first mounting structure and said slit lamp being arranged below said second mounting structure and said laser module.

* * * * *